United States Patent [19]
Marshall

[11] Patent Number: 5,928,205
[45] Date of Patent: Jul. 27, 1999

[54] MEDICAL INJECTION DEVICES

[75] Inventor: Jeremy Marshall, Jericho, United Kingdom

[73] Assignee: Owen Mumford Limited, Oxford, United Kingdom

[21] Appl. No.: 08/913,872

[22] PCT Filed: Mar. 22, 1996

[86] PCT No.: PCT/GB96/00682

§ 371 Date: Sep. 24, 1997

§ 102(e) Date: Sep. 24, 1997

[87] PCT Pub. No.: WO96/30065

PCT Pub. Date: Oct. 3, 1996

[30] Foreign Application Priority Data

Mar. 24, 1995 [GB] United Kingdom .................... 9506087

[51] Int. Cl.⁶ ................................................... A61M 5/00
[52] U.S. Cl. ........................... 604/263; 604/232; 604/192
[58] Field of Search .................................. 604/201, 192, 604/194, 195, 198, 232, 234, 263

[56] References Cited

U.S. PATENT DOCUMENTS 1,971,687  8/1934  Kratz .
2,880,723  4/1959  Adams .
3,820,652  6/1974  Thackston .

FOREIGN PATENT DOCUMENTS 2.223.051   10/1974  France .
414 953     12/1966  Switzerland .
WO 91/01152  2/1991  WIPO .

Primary Examiner—Ronald Stright
Assistant Examiner—A. T. Nguyen
Attorney, Agent, or Firm—Young & Thompson

[57] ABSTRACT

An injection device has a barrel in which a cartridge with a needle lie, the needle initially being protected by a sheath and a cap effectively closing the forward end of the barrel. The needle is on a carrier which initially is in a forward position in relation to the cartridge so that the rear end of the needle is clear of a membrane at the leading end of the cartridge. But when the cap is fitted, it pushes on the carrier and shifts it rearwardly with respect to the cartridge so that the needle penetrates the membrane. Also during fitting of the cap it engages the sheath so that, when it is removed for use of the device, the sheath is pulled off leaving the needle exposed.

9 Claims, 2 Drawing Sheets

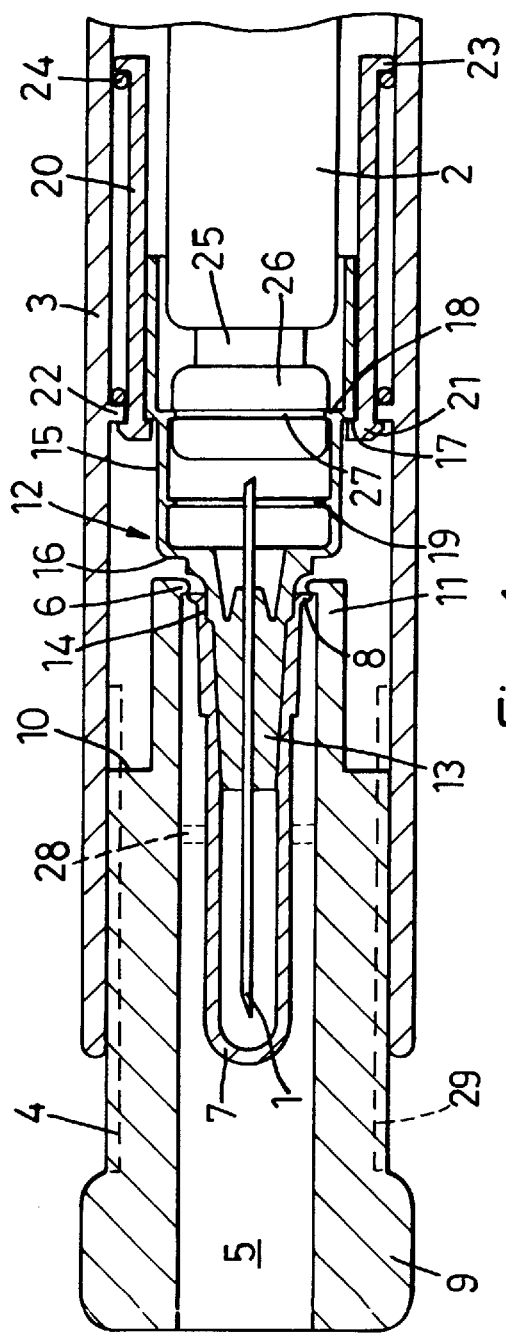
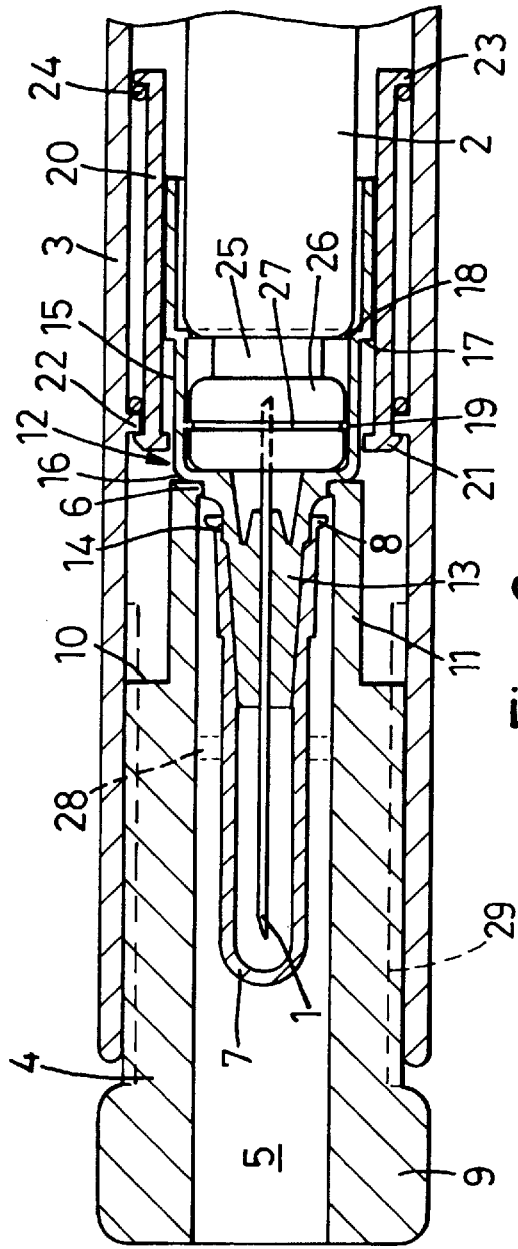

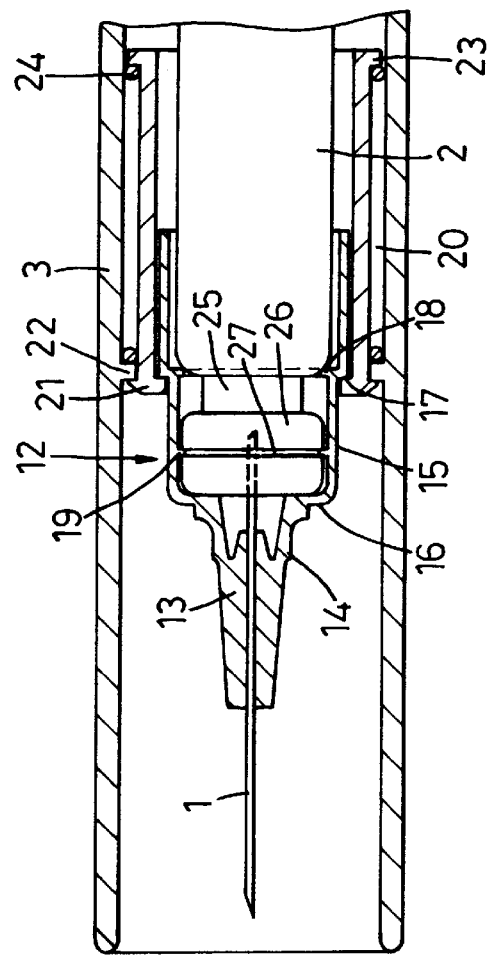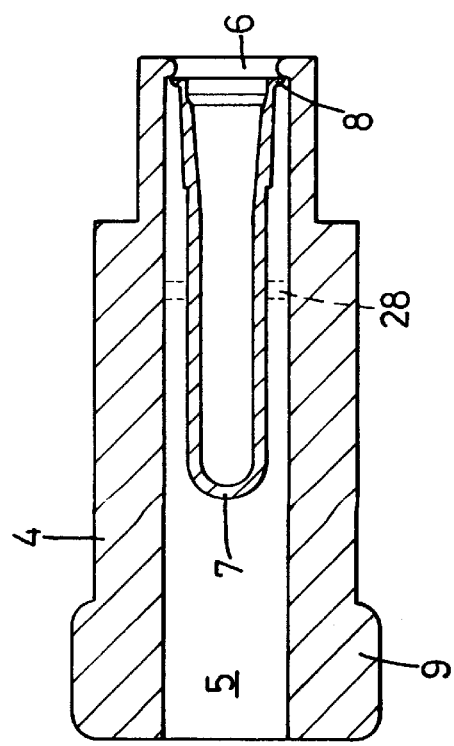
Fig. 3

MEDICAL INJECTION DEVICES

This invention relates to medical injection devices.

Some medical injection devices have a dose to be administered in a cartridge (usually known as a Schott syringe) whose leading end is closed by a membrane. The needle has a rear tip as well as a forward one, and before injection, this rear tip and the cartridge are brought together for the tip to pierce the membrane and thus open the needle passage to the fluid inside the cartridge. This application is concerned with a device in which the needle assembly is moved rearwardly to achieve the piercing, rather than one where the cartridge is shifted for that operation.

Before use, the leading tip, which is to be inserted in the patient, obviously has to be well protected. At the same time, there has to be an arrangement for pushing the needle assembly rearwardly to cause the rear tip to penetrate the membrane. While that could be done with the protection removed, that is awkward and dangerous.

It is the aim of this invention to provide an arrangement whereby the penetration of the membrane can safely be done with the needle protection still in place, that being removed afterwards just prior to injection.

According to the present invention there is provided an injection device including a barrel with a forward end cap for containing a cartridge of fluid to be injected, the cartridge being closed at its forward end by a membrane, and having a needle assembly that fits to said forward end in two modes, the first being a standby mode with the membrane intact and the second being a use mode with the membrane pierced by the rear end of the needle, the needle assembly having been shifted rearwardly with respect to the cartridge, wherein the forward end of the needle is initially protected by a sheath, and wherein the cap has a progressive application to the barrel, a first movement causing it to engage the sheath and a second movement pushing on the needle assembly to cause that to move from the first to the second mode position, subsequent removal of the cap taking the sheath off the needle to leave the device ready to use.

In other words, the cap is pushed on and then pulled off, this action automatically bringing the cartridge and the rear tip of the needle together, and then removing the protection of the forward end of the needle.

In the preferred form, the needle assembly has a snap engagement with the forward end of the cartridge in said first mode, this being released by the second movement of the cap.

The needle assembly may also have a snap fit engagement with the forward end of the cartridge in said second mode, this being achieved at the end of the second movement of the cap.

These snap engagements can each be provided by an annular rib and groove. Conveniently, the needle assembly will have two internal axially spaced annular ribs and the cartridge will have an annular groove around its leading end into which either of the ribs can engage.

Preferably, the sheath has an outward projection and the cap has an inward projection which snaps past the outward projection as the cap completes its first movement, the sheath being pulled off the needle by these projections hooking together on removal of the cap. These projections are conveniently annular ribs. Alternatively, the cap may be formed to grip the sheath by friction during its first movement and to remove the sheath by that grip.

The cap may be a push fit or a screw fit to the barrel.

For a better understanding of the invention, one embodiment will now be described, by way of example, with reference to the accompanying drawing, in which:

FIG. 1 is an axial section of the leading end of a medical injection device prior to use, FIG. 2 is an axial section of that leading end with the device being prepared for use, and FIG. 3 is an axial section of that leading end with a cap removed and the device ready for use.

The device is for administering a dose through a needle 1 from a cartridge 2. This will have a plunger (not shown) and it can itself be thrust forwards bodily to project the needle 1, the mechanism for this also not being illustrated. It does not form part of the present invention.

The needle 1 and cartridge 2 are carried co-axially within a barrel 3 whose leading end receives a cap 4 with a close sliding fit. The cap has a central longitudinal passage 5 terminating at its rear end in an internal annular rib 6 and when fitted it closely embraces a needle sheath 7 with a flared base terminating in an external annular rib 8. Externally, the cap is enlarged into a knob 9 at its outer end, and near the rear end it reduces at shoulder 10 to form a spigot 11. The end face of this spigot has a function to be described later.

The needle 1 is mounted in a carrier 12. It is actually set into a slightly coned nose 13 at whose root there is an external annular rib 14 by which the sheath 7 is gripped. The needle projects rearwardly as well as forwardly from the nose 13. To the rear of the nose, the carrier expands into a stepped cylindrical formation 15. This gives two forwardly facing outer shoulders 16 and 17, and internally registering with the rear shoulder 17 there is an annular rib 18. There is a second internal annular rib 19 between the first rib 18 and the nose 13.

An elongate collar 20 freely surrounds the rear larger diameter portion of the formation 15. At its forward end, it has a rim 21 projecting radially inwardly and outwardly to co-operate respectively with the shoulder 17 and the forward side of an annular rib 22 on the inside of the barrel 3. At its rear end, the collar has an outward flange 23 and a coil spring 24 surrounding the collar acts between that flange and the rear side of the rib 22.

The cartridge 2 has at its leading end a neck 25 and a head 26 around which there is an annular groove 27.

In the initial position, as shown in FIG. 1, the rib 18 engages in the groove 27 to hold the needle carrier 12 firmly to the cartridge 2 in such a way that the rear tip of the needle 1 is clear of the cartridge. The cap 5 is pushed in to an intermediate position where the internal rib 6 snaps past the external rib 8, leaving the end face of the spigot 11 just clear of or lightly abutting the shoulder 16 where the cylindrical formation 15 reduces towards the nose 13. In that position, there is resistance to further pushing in of the cap provided by the cartridge-needle assembly.

To make the injector ready for use, the cap 5 is pressed by the knob 8 further into the barrel 3. The end face of the spigot 11 then engages the shoulder 16 and pushes the needle carrier 12 rearwardly. The rib 18 snaps out of the groove 27, and when the cap 5 is fully home, the rib 19 snaps into the groove 27. During this movement, the rear tip of the needle 1 penetrates the membrane at the leading end of the cartridge 2. The device is then in the FIG. 2 position.

For use, the cap 5 is pulled away as shown in FIG. 3. The needle carrier 12 is retained closed up to the cartridge 2 by the rib 19 engaged in the groove 27, but the mutual hooking of the ribs 6 and 8 is sufficiently tenacious to snap the sheath 7 clear of the rib 14 and take the sheath away with the cap. The cartridge-needle assembly will then have moved forwards for the shoulder 17 to abut and be arrested by the rim 21, although the spring 24 may compress a bit before the sheath is released.

An alternative way for the cap 4 to grip the sheath 7 is by an annular rib 28, indicated by broken lines in the Figures, at an intermediate position in the passage 5 so that it will be just forward of the nose 13. The rib 6 will not then be provided. With a rubber or suitable plastics sheath 7, and with the rib 28 dimensioned to engage it firmly, even to the extent of nipping it in slightly, there will be sufficient friction for the sheath to be pulled off when the cap is removed.

Instead of pushing the cap into the forward end of the barrel, it may have screw-threaded engagement as shown at 29 in FIGS. 1 and 2. The knob 9 is therefore rotated rather than pushed.

I claim:

1. An injection device including a cartridge (2) of fluid to be injected, the cartridge (2) being closed at its forward end by a membrane, and having a needle assembly (12) that fits to said forward end in two modes, the first being a standby mode with the membrane intact and the second being a use mode with the membrane pierced by the rear end of the needle (1), the needle assembly (12) having been shifted rearwardly with respect to the cartridge (2), wherein the forward end of the needle (1) is initially protected by a sheath (7), characterised in that the device further comprises a barrel (3) with a forward end cap (4) for containing the cartridge and in that the cap (4) has a progressive application to the barrel (3), a first movement causing it to engage the sheath (7) and a second movement pushing on the needle assembly (12) to cause that to move from the first to the second mode position, subsequent removal of the cap (4) taking the sheath (7) off the needle to leave the device ready to use.

2. An injection device as claimed in claim 1, characterised in that the needle assembly (12) has a snap fit engagement with the forward end of the cartridge (2) in said first mode, this being released by the second movement of the cap (4).

3. An injection device as claimed in claim 1 characterised in that the needle assembly (12) has a snap fit engagement with the forward end of the cartridge (2) in said second mode, this being achieved at the end of the second movement of the cap (4).

4. An injection device as claimed in claim 2, characterised in that the needle assembly (12) has two internal axially spaced annular ribs (18, 19) and the cartridge (2) has an annular groove (27) around its leading end into which either of the ribs (18,19) can engage.

5. An injection device as claimed in claim 1, characterised in that the sheath (7) has an outward projection (8) and the cap (4) has an inward projection (6) which snaps past the outward projection as the cap (4) completes its first movement, the sheath (7) being pulled off the needle (1) by these projections (6,8) hooking together on removal of the cap (4).

6. An injection device as claimed in claim 5, characterised in that the projections (6,8) are annular ribs.

7. An injection device as claimed in claim 1, characterised in that the cap (4) is formed (28) to grip the sheath (7) by friction during its first movement, and to remove the sheath (7) by that grip.

8. An injection device as claimed in claim 1, characterised in that the cap (4) is a push fit to the barrel (3).

9. An injection device as claimed in claim 1, characterised in that the cap (4) is a screw fit to the barrel (3).

* * * * *